US012778490B2

(12) United States Patent
Ihns

(10) Patent No.: US 12,778,490 B2
(45) Date of Patent: Nov. 3, 2026

(54) METHOD AND APPARATUS FOR ASSISTING DERMATOLOGICAL DIAGNOSIS

(71) Applicant: Jurgen R. Ihns, Gulf Breeze, FL (US)

(72) Inventor: Jurgen R. Ihns, Gulf Breeze, FL (US)

( * ) Notice: Subject to any disclaimer, the term of this patent is extended or adjusted under 35 U.S.C. 154(b) by 350 days.

(21) Appl. No.: 18/695,119

(22) PCT Filed: Sep. 23, 2022

(86) PCT No.: PCT/US2022/044588
§ 371 (c)(1),
(2) Date: Aug. 21, 2024

(87) PCT Pub. No.: WO2023/049384
PCT Pub. Date: Mar. 30, 2023

(65) Prior Publication Data

US 2025/0099023 A1 Mar. 27, 2025

Related U.S. Application Data

(60) Provisional application No. 63/248,468, filed on Sep. 25, 2021.

(51) Int. Cl.
*A61B 5/00* (2006.01)

(52) U.S. Cl.
CPC ............ *A61B 5/441* (2013.01); *A61B 5/0077* (2013.01); *A61B 5/7264* (2013.01)

(58) Field of Classification Search
CPC ..... A61B 5/441; A61B 5/0077; A61B 5/7264; A61B 5/0075; G01N 2201/0627; G01N 2201/1296; G01N 21/31
See application file for complete search history.

(56) References Cited

U.S. PATENT DOCUMENTS 6,081,612 A 6/2000 Gutkowicz-Krusin et al.
2011/0301441 A1* 12/2011 Bandic ................ A61B 5/4875 600/306

(Continued)

FOREIGN PATENT DOCUMENTS

WO WO 2020/146489 A1 7/2020
WO WO-2021165771 A1 * 8/2021 ....... A61B 1/000096

OTHER PUBLICATIONS

Hosking et al.: "Hyperspectral Imaging in Automated Digital Dermoscopy Screening for Melanoma"; Lasers in Surgery and Medicine; 2019.

(Continued)

*Primary Examiner* — Joel Lamprecht
(74) *Attorney, Agent, or Firm* — Bryan W. Bockhop; Bockhop Intellectual Property Law, LLC

(57) ABSTRACT

An apparatus (100) for assisting diagnosis of a dermatological phenomenon (12) includes a variable wavelength light source (110). A camera (120) captures images of the dermatological phenomenon (12). A computer (130) controls the variable wave-length light source (110) and the camera (120). The computer (130) is programmed to: cause the light source (110) to illuminate the dermatological phenomenon with different wavelengths each at different times; capture an image of the dermatological phenomenon illuminated with each of the different wavelengths to generate a set of images (140); execute a neural network that has been trained with images of dermatological phenomena types with the set of images (140) to generate a probability that the set of images (140) corresponds to a selected phenomenon type; and indicate the probability that the dermatological phenomenon (12) corresponds to at least one of dermatological phenomena types.

16 Claims, 1 Drawing Sheet

(56) References Cited

U.S. PATENT DOCUMENTS

| | | | |
|---|---|---|---|
| 2020/0193597 A1 | 6/2020 | Fan et al. | |
| 2020/0237317 A1 | 7/2020 | Newberry et al. | |
| 2021/0169400 A1* | 6/2021 | Fan | A61B 5/0064 |

OTHER PUBLICATIONS

Haenssle et al.: "Man against machine: diagnostic performance of a deep learning convolutional neural network for dermoscopic melanoma recognition in comparison to 58 dermatologists"; Annals of Oncology; May 8, 2018; Oxford University Press.

European Patent Office: "Supplementary European Search Report"; May 21, 2025 (Search report in related European case, Serial No. EP 22 87 3655).

European Patent Office: "Communication pursuant to Article 94(3) EPC"; Oct. 6, 2026; (Office Action in corresponding European patent application).

* cited by examiner

METHOD AND APPARATUS FOR ASSISTING DERMATOLOGICAL DIAGNOSIS

BACKGROUND OF THE INVENTION

1. Field of the Invention

The present invention relates to dermatological diagnosis methods and apparatus and, more specifically, for a non-invasive method and apparatus for assisting in making a dermatological diagnosis.

2. Description of the Related Art

Physicians, such as dermatologists, use a variety of tools to diagnose suspect dermatological phenomena, such as masses, lesions and tumors. Usually, a visual inspection of a suspect phenomenon is performed. Based on such an inspection, a physician might rule out certain conditions like melanoma when the suspect phenomenon appears as an ordinary mole in shape and color. However, some melanomas can mimic a mole in shape, symmetry and color, which might result in a misleading diagnosis.

Generally, a common mole resides on the surface of the epidermis. A melanoma, on the other hand, often extends through the epidermis into the dermis, sometimes more than 4 mm below the surface of the skin.

Current diagnostic methods for melanoma include a visual examination and a physician review of a patient's health history. A biopsy is taken when the visual examination and history indicate a higher risk. However, a physician might be reluctant to take a biopsy of what appears to be a common mole for reasons of cost and patient discomfort.

Therefore, there is a need for an inexpensive non-invasive tool to assist a physician in diagnosing melanoma and other dermatological phenomena.

SUMMARY OF THE INVENTION

The disadvantages of the prior art are overcome by the present invention which, in one aspect, is an apparatus, method and system for assisting dermatological diagnosis. The system illuminates a dermatological phenomenon with a plurality of lights of different wavelengths and captures images of the phenomenon at each wavelength. Each wavelength penetrates skin to a different depth and, therefore, each image is of the phenomenon at a different depth. The resulting set of images is processed by an artificial intelligence system, such as a convolutional neural network, which is trained to generate probabilities of the phenomenon being classified as belonging to each of a set of different diagnoses.

In another aspect, the invention is an apparatus for assisting diagnosis of a dermatological phenomenon, that includes a variable wavelength light source. A camera captures images of the dermatological phenomenon. A computer controls the variable wavelength light source and the camera. The computer programmed to: cause the variable wavelength light source to illuminate the dermatological phenomenon with a plurality of different wavelengths each at a corresponding plurality of different times; capture an image of the dermatological phenomenon illuminated with each of the plurality of different wavelengths at each different time so as to generate a set of images; execute a neural network that has been trained with images of a plurality of dermatological phenomena types with the set of images so as to generate a probability that the set of images corresponds to a selected phenomenon type of the plurality of dermatological phenomena types; and display an indication of a probability that the dermatological phenomenon corresponds to at least one of dermatological phenomena types.

In yet another aspect, the invention is a method of assisting diagnosis of a dermatological phenomenon, in which the dermatological phenomenon is illuminated with a plurality of different wavelengths at a corresponding plurality of different times. An image of the dermatological phenomenon illuminated with each of the plurality of different wavelengths is captured at each different time so as to generate a set of images. A neural network is executed. The neural network has been trained with images of a plurality of dermatological phenomena types with the set of images, thereby generating a probability that the set of images corresponds to a selected phenomenon type of the plurality of dermatological phenomena types. An indication of a probability that the dermatological phenomenon corresponds to at least one of dermatological phenomena types is displayed.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1A:
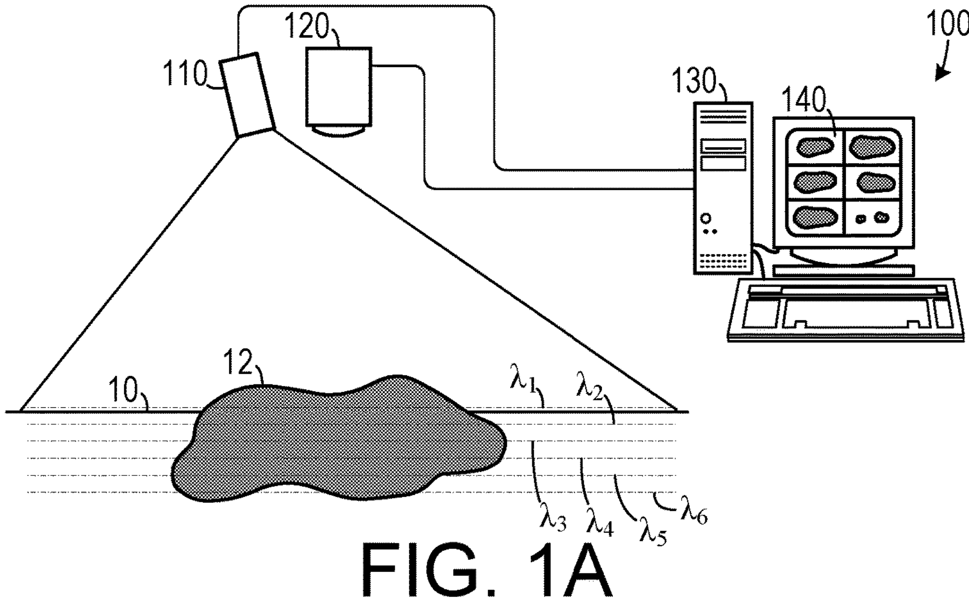
FIG. 1A is a schematic diagram of an apparatus for assisting dermatological diagnosis in use.

A preferred embodiment of the invention is now described in detail. Referring to the drawings, like numbers indicate like parts throughout the views. Unless otherwise specifically indicated in the disclosure that follows, the drawings are not necessarily drawn to scale. The present disclosure should in no way be limited to the exemplary implementations and techniques illustrated in the drawings and described below. As used in the description herein and throughout the claims, the following terms take the meanings explicitly associated herein, unless the context clearly dictates otherwise: the meaning of "a," "an," and "the" includes plural reference, the meaning of "in" includes "in" and "on." Also, as used herein, "global computer network" includes the Internet.

Figure 1B:
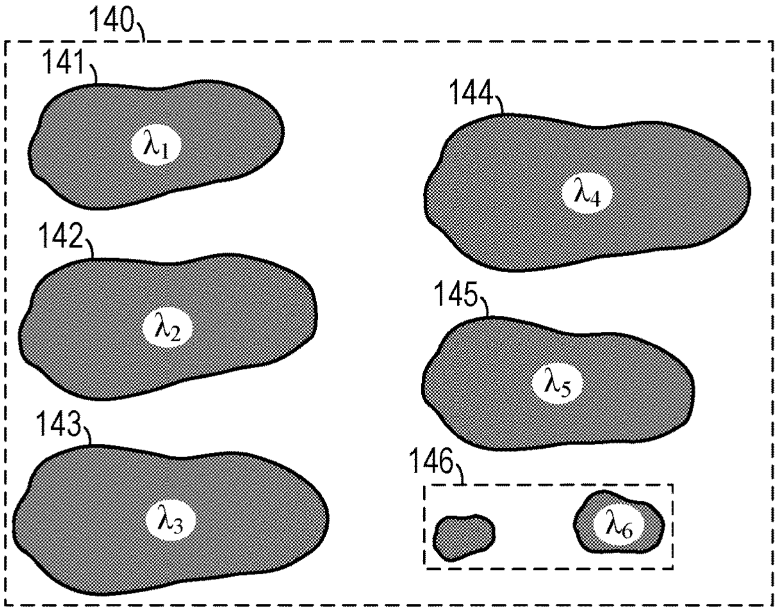
FIG. 1B is a set of schematic images captured by the apparatus shown in FIG. 1A.

As shown in FIGS. 1A and 1B, one embodiment of an apparatus 100 for assisting dermatological diagnosis includes a variable wavelength light source 110 that is controlled by a computer 130. The variable wavelength light source 110 (e.g., a tunable light emitting diode or an array of light emitting diodes, each of which generates light of a different wavelength) is able to generate light at a plurality of different wavelengths wherein each of the plurality of wavelengths penetrate skin to a different depth. For example, light having a wavelength of 415 nm will penetrate to about 0.1 mm into the epidermis; light having a wavelength of 450 nm will penetrate to about 0.3 mm, which is around the interface between the epidermis and the dermis; light having a wavelength of 525 nm will penetrate into the dermis to a depth of about 2.0 mm from the surface of the skin; light having a wavelength of 590 nm will penetrate to about 2.5 mm from the surface of the skin; light having a wavelength of 633 nm will penetrate to about 3.0 mm from the surface of the skin, which is near the bottom of the dermis; and light having a wavelength of 830 nm will penetrate into the subcutaneous layer. The light source 110 can include, for example, an array of light emitting diodes that are each tuned to one the desired wavelengths. The variable wavelength light source 110 is directed to the surface 10 of the patient's skin so as to illuminate the entire phenomenon of interest 12.

A camera 120 (e.g., a CMOS camera, a scientific CMOS camera, a charge-coupled device camera, etc.) captures images of the phenomenon of interest 12 while illuminated at each of the different wavelengths. Each captured image 140 is of the phenomenon of interest 12 illuminated at a different wavelength, which includes image data of the phenomenon of interest 12 at a different depth. For example, illuminating the phenomenon of interest 12 with light of wavelength $\lambda_1$ results in image 141; illuminating it with light of wavelength $\lambda_2$ results in image 142; illuminating it with light of wavelength $\lambda_3$ results in image 143; illuminating it with light of wavelength $\lambda_4$ results in image 144; illuminating it with light of wavelength $\lambda_5$ results in image 145; and illuminating it with light of wavelength $\lambda_6$ results in image 146.

The computer 130 employs an artificial intelligence (AI) system, such as a convolutional neural network (CNN). The CNN can run on the computer (typically on a graphics processing unit) or can run on a remote mainframe via the global computer network. The CNN is trained with sets of images of various dermatological phenomena in which each set is labelled according to the type of phenomenon it represents. For example, the CNN can be trained with sets of images of basal cell carcinoma, sets of images of melanoma, sets of images of squamous cell carcinoma, sets of images of Merkel cell carcinoma, sets of images of atypical moles, sets of images of typical moles, etc. More sets of images of each type of phenomenon that are used to train the CNN will deliver a better result.

Figure 2:
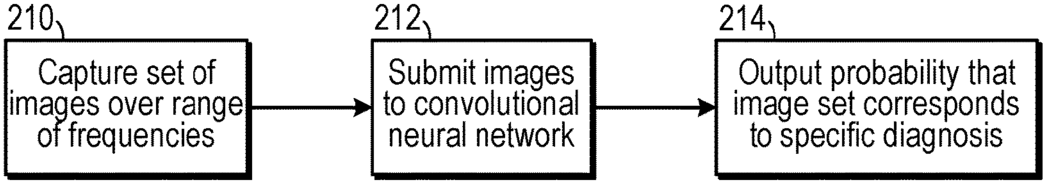
FIG. 2 is a flow diagram showing steps performed by the apparatus shown in FIG. 1A.

As shown in FIG. 2, images of the phenomenon are captured over a range of frequencies 210 which results in a set of images of the phenomenon at different depths. The CNN (or other image processing AI system) processes the set of images 212 and the CNN generates a probability that the set of images corresponds to a labelled phenomenon type with which the CNN was trained.

For example, when a set of images from a patient is processed by the CNN, the CNN could return the following probabilities: p(basal cell carcinoma)=0.05; p(melanoma)=0.13; p(squamous cell carcinoma)=0.06; p(Merkel cell carcinoma)=0.03; p(atypical moles)=0.68; and p(typical moles)=0.05. These probabilities would indicate that the set of images conforms most closely to those of atypical moles and that the next-most likely candidate would be melanoma. Using this information, a clinician would concentrate his or her investigation by using tools for diagnosing atypical moles and melanoma.

This system uses image data from different depths, thereby using more information than what would be available through surface visual inspection alone. Such information could be highly valuable in assisting the clinician in distinguishing between a typical mole and cancerous mass that appears like a typical mole.

Although specific advantages have been enumerated above, various embodiments may include some, none, or all of the enumerated advantages. Other technical advantages may become readily apparent to one of ordinary skill in the art after review of the following figures and description. It is understood that, although exemplary embodiments are illustrated in the figures and described below, the principles of the present disclosure may be implemented using any number of techniques, whether currently known or not. Modifications, additions, or omissions may be made to the systems, apparatuses, and methods described herein without departing from the scope of the invention. The components of the systems and apparatuses may be integrated or separated. The operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. It is intended that the claims and claim elements recited below do not invoke 35 U.S.C. § 112(f) unless the words "means for" or "step for" are explicitly used in the particular claim. The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. An apparatus for assisting diagnosis of a dermatological phenomenon, comprising:

(a) a variable wavelength light source;

(b) a camera that captures images of the dermatological phenomenon; and (c) a computer that controls the variable wavelength light source and the camera, the computer programmed to:

(i) cause the variable wavelength light source to illuminate the dermatological phenomenon with a plurality of different wavelengths each at a corresponding plurality of different times wherein each of the different wavelengths penetrates skin to a different depth;

(ii) capture an image of the dermatological phenomenon illuminated with each of the plurality of different wavelengths at each different time so as to generate a set of images, wherein each image of the set of images is of the dermatological phenomenon at a different depth;

(iii) train a neural network with a plurality of images, wherein each of the plurality of images is labelled as a selected one of: basal cell carcinoma, melanoma, squamous cell carcinoma, Merkel cell carcinoma, atypical moles or typical moles;

(iv) process the set of images with the neural network so as to generate a plurality of probabilities, including: a probability that the set of images corresponds to basal cell carcinoma, a probability that the set of images corresponds to melanoma, a probability that the set of images corresponds to squamous cell carcinoma, a probability that the set of images corresponds to Merkel cell carcinoma, a probability that the set of images corresponds to atypical moles, and a probability that the set of images corresponds to typical moles; and (v) display each of the plurality of probabilities.

2. The apparatus of claim 1, wherein the variable wavelength light source comprises a wavelength tunable light emitting diode.

3. The apparatus of claim 1, wherein the variable wavelength light source comprises an array of different light emitting diodes in which each diode generates light of a different wavelength.

4. The apparatus of claim 1, wherein the camera comprises a CMOS camera.

5. The apparatus of claim 1, wherein the neural network comprises a convolutional neural network.

6. An apparatus for assisting diagnosis of a dermatological phenomenon, comprising:

(a) a variable wavelength light source that includes at least one wavelength tunable light emitting diode;

(b) a camera that captures images of the dermatological phenomenon; and (c) a computer that controls the variable wavelength light source and the camera, the computer programmed to:

(i) cause the variable wavelength light source to illuminate the dermatological phenomenon with a plurality of different wavelengths each at a corresponding plurality of different times wherein each of the different wavelengths penetrates skin to a different depth;

(ii) capture an image of the dermatological phenomenon illuminated with each of the plurality of different wavelengths at each different time so as to generate a set of images, wherein each image of the set of images is of the dermatological phenomenon at a different depth;

(iii) train a neural network with a plurality of images, wherein each of the plurality of images is labelled as a selected one of: basal cell carcinoma, melanoma, squamous cell carcinoma, Merkel cell carcinoma, atypical moles or typical moles; and (iv) process the set of images with the neural network so as to generate a plurality of probabilities, including: a probability that the set of images corresponds to basal cell carcinoma, a probability that the set of images corresponds to melanoma, a probability that the set of images corresponds to squamous cell carcinoma, a probability that the set of images corresponds to Merkel cell carcinoma, a probability that the set of images corresponds to atypical moles, and a probability that the set of images corresponds to typical moles; and (v) display each of the plurality of probabilities.

7. The apparatus of claim 6, wherein the tunable light emitting diode comprises an array of different light emitting diodes in which each diode generates light of a different wavelength.

8. The apparatus of claim 6, wherein the camera comprises a CMOS camera.

9. The apparatus of claim 6, wherein the neural network comprises a convolutional neural network.

10. A method of assisting diagnosis of a dermatological phenomenon on skin, comprising the steps of:

(a) illuminating the dermatological phenomenon with a plurality of different wavelengths at a corresponding plurality of different times, wherein each of the different wavelengths penetrates the skin to a different depth;

(b) capturing an image of the dermatological phenomenon illuminated with each of the plurality of different wavelengths at each different time so as to generate a set of images, wherein each image of the set of images is of the dermatological phenomenon at a different depth;

(c) training a neural network with a plurality of images, wherein each of the plurality of images is labelled as a selected one of: basal cell carcinoma, melanoma, squamous cell carcinoma, Merkel cell carcinoma, atypical moles or typical moles;

(d) processing the set of images with the neural network so as to generate a plurality of probabilities, including: a probability that the set of images corresponds to basal cell carcinoma, a probability that the set of images corresponds to melanoma, a probability that the set of images corresponds to squamous cell carcinoma, a probability that the set of images corresponds to Merkel cell carcinoma, a probability that the set of images corresponds to atypical moles, and a probability that the set of images corresponds to typical moles; and (e) displaying each of the plurality of probabilities.

11. The method of claim 10, wherein the illuminating step employs a variable wavelength light source.

12. The method of claim 11, wherein the variable wavelength light source comprises a wavelength tunable light emitting diode and wherein the illuminating step further comprises the step of tuning tunable light emitting diode to a different wavelength at each of the different times.

13. The method of claim 11, wherein the variable wavelength light source comprises an array of different light emitting diodes and wherein the illuminating step further comprises the step of activating a different one of the different light emitting diodes at each of the different times.

14. The method of claim 10, wherein the step of capturing an image comprises capturing the image with a computer controlled camera.

15. The method of claim 14, wherein the camera comprises a CMOS camera.

16. The method of claim 10, wherein the neural network comprises a convolutional neural network.

* * * * *